United States Patent
Mendrok-Edinger et al.

(10) Patent No.: US 11,306,054 B2
(45) Date of Patent: Apr. 19, 2022

(54) PROPANEDIOL MONOACETATE MONONITRATE

(71) Applicant: DSM IP ASSETS B.V., Heerlen (NL)

(72) Inventors: Christine Mendrok-Edinger, Kaiseraugst (CH); Peter Riebel, Kaiseraugst (CH); Angela Wildermann, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 129 days.

(21) Appl. No.: 16/770,730

(22) PCT Filed: Dec. 11, 2018

(86) PCT No.: PCT/EP2018/084299
§ 371 (c)(1),
(2) Date: Jun. 8, 2020

(87) PCT Pub. No.: WO2019/115503
PCT Pub. Date: Jun. 20, 2019

(65) Prior Publication Data
US 2021/0163396 A1 Jun. 3, 2021

(30) Foreign Application Priority Data
Dec. 13, 2017 (EP) .................................... 17207065

(51) Int. Cl.
| C07C 203/04 | (2006.01) |
| A61P 17/10 | (2006.01) |
| A61P 31/04 | (2006.01) |
| A61K 8/40 | (2006.01) |
| A61Q 17/00 | (2006.01) |
| A61Q 5/00 | (2006.01) |
| A61Q 15/00 | (2006.01) |
| A61Q 19/00 | (2006.01) |

(52) U.S. Cl.
CPC .............. *C07C 203/04* (2013.01); *A61K 8/40* (2013.01); *A61P 17/10* (2018.01); *A61P 31/04* (2018.01); *A61Q 17/005* (2013.01); *A61Q 5/006* (2013.01); *A61Q 15/00* (2013.01); *A61Q 19/00* (2013.01)

(58) Field of Classification Search
CPC ........ A61Q 19/00; A61Q 17/005; A61P 31/04
See application file for complete search history.

(56) References Cited

U.S. PATENT DOCUMENTS

2015/0328323 A1* 11/2015 Satyam .................. A61K 47/48

FOREIGN PATENT DOCUMENTS

| JP | 2014/055138 | 3/2014 | |
| WO | WO2007095261 A2 * | 7/2007 | ............ A61K 8/345 |
| WO | 2007/095261 | 8/2007 | |
| WO | 2011/047421 | 4/2011 | |

OTHER PUBLICATIONS

International Search Report for PCT/EP2018/084299, dated Mar. 4, 2019, 3 pages.
Written Opinion of the ISA for PCT/EP2018/084299, dated Mar. 4, 2019, 5 pages.

* cited by examiner

*Primary Examiner* — Mark V Stevens
*Assistant Examiner* — Alparslan Asan
(74) *Attorney, Agent, or Firm* — Nixon & Vanderhye P.C.

(57) ABSTRACT

The present invention relates to propanediol monoacetate mononitrate as well as the use thereof as antimicrobial agent, in particular for cosmetic applications.

18 Claims, No Drawings

PROPANEDIOL MONOACETATE MONONITRATE

This application is the U.S. national phase of International Application No. PCT/EP2018/084299 filed 11 Dec. 2018 which designated the U.S. and claims priority to EP Patent Application No. 17207065.8 filed 13 Dec. 2017, the entire contents of each of which are hereby incorporated by reference.

The present invention relates to propanediol monoacetate mononitrate as well as the use thereof as antimicrobial agent, in particular for cosmetic applications.

Antimicrobial active compounds play a key role for many cosmetic applications:

Acne is taken to mean a skin disorder which is evident in inflamed papules, pustules or nodules, caused by increased talc production and impaired keratinization of the skin. The inflammation may be associated with reddening, swelling and pressure pain. Besides genetic predisposition, potential causes of acne formation can be androgens, comedogenic substances (for example in cosmetics), smoking, stress or excessive colonization of the skin by bacteria. Acne can be triggered, for example, by microorganisms, such as *Propionibacterium acnes*, or *Staphylococcus epidermidis*. *Propionibacterium acnes* is a bacterium which usually colonizes the skin and lives on sebum. Acne may arise, for example, if the number of these bacteria is increased. The presence of bacteria in the follicles results in inflammation reactions, which is evident in the form of red nodules or pustules. The production of free fatty acids by the bacteria furthermore promotes the inflammation reaction in the follicle.

Besides water and salt, axillary sweat contains many other substances (such as fats, amino acids, sugars, lactic acid, urea, etc.). Freshly formed sweat is odorless; the typical sweat odor only forms due to the action of skin bacteria on the sweat, which decompose the latter. Examples of such bacteria are *Staphylococcus* spp or *Corynebacterium* pp. For this reason, antimicrobial substances are usually also employed besides aroma substances and antiperspirants in deodorants, with the aim of controlling the bacteria which are involved in the odor formation.

The fungal genus *Malassezia* comprises lipid-dependent and lipophilic yeast species that are part of the normal skin microbiota. In general, because of their dependence on lipids for survival, *Malassezia* yeasts are most often found in sebum-rich areas of the skin such as the trunk, back, face, and scalp. Several adverse skin conditions have been associated with an overpopulation of *Malassezia* yeasts such as itching skin, *Pityriasis versicolor*, dandruff formation, seborrheic dermatitis atopic dermatitis, and psoriasis.

Surprisingly, it has now been found that the novel compound propanediol monoacetate mononitrate exhibits an excellent antimicrobial activity against several cosmetically relevant microorganisms such as *S. epidermis, M. furfur, P. acnes* and *C. xerosis* and is thus particularly suitable as cosmetic ingredient for treating adverse effects resulting from an overpopulation thereof.

Thus, in a first embodiment, the present invention relates to propanediol monoacetate mononitrate of formula (I)

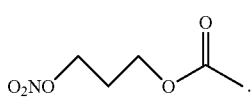

(I)

(i.e. 1,3-propanediol monoacetate mononitrate also referred to as PDMAMN).

In a second embodiment, the present invention relates to the use of propanediol monoacetate mononitrate as antimicrobial agent, i.e. an agent which exhibits an antimicrobial activity. In particular the present invention is directed to the use of propanediol monoacetate mononitrate as anti-fungal and/or anti-bacterial agent, more in particular as an agent for killing and/or inhibiting the growth of fungi and/or gram positive or gram negative bacteria such as in particular *Staphylococcus epidermis* (*S. epidermis*), *Corynebacterium xerosis*, (*C. xerosis*), *Malessazia furfur* (*M. furfur*) and/or *Propionibacterium acnes* (*P. acnes*).

In another embodiment, the invention relates to a method for killing and/or inhibiting growth of microbial cells, in particular fungal and/or bacterial cells, said method comprising contacting said microbial cells with propanediol monoacetate mononitrate. In a preferred embodiment, the microbial cells are selected from the group consisting of fungi and/or gram-positive or gram-negative bacteria, more preferably from the group consisting of *S. epidermis, C. xerosis, M. furfur* and *P. acnes* as well as mixtures thereof.

Propanediol monoacetate mononitrate can be prepared according to standard methods in the art such as by reacting 1,3-propandiol monoacetate (PDMA) in dichloromethane with nitrosulfuric acid as illustrated in the examples.

The term "antimicrobial activity" (or "antimicrobial effect") as used herein means a capability of killing and/or inhibiting the growth of microbial cells such as in particular of bacteria and fungi and more in particular of *S. epidermis, C. xerosis, M. furfur* and *P. acnes* as well as mixtures thereof. Preferably, the antimicrobial activity is used for non-therapeutic purpose/in non-therapeutic, e.g. cosmetic applications.

Due to its antimicrobial activity against *S. epidermis, C. xerosis, M. furfur* and *P. acnes* propanediol monoacetate mononitrate is suitable to maintain skin homeostasis and/or balance the skin microbiome by treating overpopulation of such microorganisms on the skin. Thus, the present invention also relates to the (non-therapeutic) use of propanediol monoacetate mononitrate to maintain skin homeostasis and/or balance the skin microbiome. Furthermore, the invention relates to a method to maintain skin homeostasis and/or balance the skin microbiome, said method comprising applying a cosmetic or pharmaceutical composition comprising an effective amount of propanediol monoacetate mononitrate to the skin.

Due to its activity against *P. acnes* (acne control application), *S. epidermis* and/or *C. xerosis* (antiperspirant/deodorant applications) and *M furfur* (dandruff, itching skin) the present invention furthermore relates to the use of propanediol monoacetate mononitrate as anti-acne, deodorant or anti-dandruff active compound.

Particularly advantageous is the use of propanediol monoacetate mononitrate as active compound for the treatment or prophylaxis of acne which is triggered by P. *Acnes* and/or *S. epidermidis*.

Also advantageous is the use of propanediol monoacetate mononitrate as active compound in deodorants or antiperspirant products as it has an antimicrobial action against the bacteria which are responsible for the decomposition of sweat and thus for the formation of the odour, i.e. against *S. epidermis* and *C. xerosis*.

Further advantageous is propanediol monoacetate mononitrate used for the treatment, prevention and/or prophylaxis of any disorder and disease where it is desirable to kill and/or inhibit the growth of *Malassezia* yeasts such as in particular *Malassezia furfur* in a patient in need thereof such as e.g. for the treatment, prevention and/or prophylaxis of *Pityriasis versicolor*, dandruff formation, seborrheic dermatitis, atopic dermatitis and psoriasis.

To make use of the anti-microbial activity of propanediol monoacetate mononitrate it is preferably incorporated into a cosmetic or pharmaceutical composition.

The amount of propandiol monoacetate mononitrate in the cosmetic or pharmaceutical compositions according to the present invention is preferably selected in the range of about 0.005 to 2 wt.-%, preferably 0.01 to 1 wt.-%, more preferably in the range of about 0.05 to 0.75 wt.-% and most preferably in the range of 0.1 to 0.5 wt.-%, based on the total weight of the composition.

Propanediol monoacetate mononitrate can be used as such or in the form in dilution with an appropriate solvent. Suitable solvents include in particular any solvent used in cosmetic and/or pharmaceutical compositions such as preferably propyleneglycol, butyleneglycol, polyethylene glycol (e.g. PEG 400).

If used in solution, Propanediol monoacetate mononitrate is preferably contained therein in an amount of 1 to 20 wt.-%, based on the total weight of the solution.

The use according to the invention of propanediol monoacetate mononitrate can take place both in the cosmetic sense and in the pharmaceutical sense. A pharmaceutical application is conceivable, for example, in the case of anti-acne compositions. In all embodiments of the present invention, the use is however preferably cosmetic (non-therapeutic).

The cosmetic or pharmaceutical compositions according to the present invention are in particular topically applied to mammalian keratinous tissue such as in particular to human skin or the human scalp.

The term "cosmetic composition" as used in the present application refers to cosmetic compositions as defined under the heading "Kosmetika" in Römpp Lexikon Chemie, 10th edition 1997, Georg Thieme Verlag Stuttgart, New York as well as to cosmetic compositions as disclosed in A. Domsch, "Cosmetic Compositions", Verlag für chemische Industrie (ed. H. Ziolkowsky), $4^{th}$ edition, 1992.

The compositions according to the present invention are generally prepared by admixing propanediol monoacetate mononitrate (pure or as solution) in an amount selected in the range of about 0.001 to 2 wt.-%, more preferably in the range of about 0.005 to 1 wt.-%, most preferably in the range of about 0.01 to 0.75 wt.-% such as in the range of 0.1 to 0.5 wt.-%, based on the total weight of the composition with a cosmetically or pharmaceutically acceptable carrier.

The term cosmetically or pharmaceutically acceptable carrier refers to a physiologically acceptable medium, i.e. a medium compatible with keratinous substances, such as the skin, mucosa, and keratinous fibers and encompasses all carriers and/or excipients and/or diluents conventionally used in cosmetic compositions or pharmaceutical compositions.

Preferably, the cosmetic or pharmaceutical compositions according to the invention are in the form of a suspension or dispersion in solvents or fatty substances, or alternatively in the form of an emulsion or micro emulsion (in particular of O/W- or W/O-type), PIT-emulsion, nano emulsion, multiple emulsion (e. g. O/W/O- or W/O/W-type), pickering emulsion, hydrogel, lipogel, one- or multiphase solution or vesicular dispersion.

The cosmetic or pharmaceutical compositions in accordance with the invention can be in the form of a liquid, lotion, a thickened lotion, a gel, a cream, a milk, an ointment or a paste.

The cosmetic or pharmaceutical compositions according to the invention have a pH in the range of 3-10, preferably in the range of pH of 3-8, most preferred in the range of pH 3.5-7.5. The pH is adjusted by methods known to a person skilled in the art, e.g. by using an acid such as a hydroxy acid including glycolic acid, lactic acid, malic acid, citric acid and tartaric acid or a base such as e.g. as e.g. sodium or potassium hydroxide, GT ammonium hydroxide or amines such as triethanolamine or tromethamine as well as mixtures thereof.

The cosmetic compositions according to the present invention are in particular skin care preparations, functional preparations and/or hair care preparations such as most in particularly skin or hair care preparations.

Examples of skin care preparations are, in particular, light protective preparations (sun care preparations), anti-ageing preparations, preparations for the treatment of photo-ageing, body oils, body lotions, body gels, treatment creams, skin protection ointments, moisturizing preparations such as moisturizing gels or moisturizing sprays, face and/or body moisturizers, as well as skin lightening preparations.

Preferably in all embodiments of the present invention the skin care preparation is a deodorant, an anti-perspirant, or an anti-acne composition.

Examples of functional preparations are cosmetic compositions containing active ingredients such as hormone preparations, vitamin preparations, vegetable extract preparations, anti-ageing preparations, and/or antimicrobial (anti-bacterial or antifungal) preparations without being limited thereto.

Examples of hair care preparations which are suitable according to the invention and which may be mentioned are shampoos, hair conditioners (also referred to as hair rinses), hairdressing compositions, hair tonics, hair regenerating compositions, hair lotions, water wave lotions, hair sprays, hair creams, hair gels, hair oils, hair pomades or hair brilliantines. Accordingly, these are always preparations which are applied to the hair and the scalp for a shorter or longer time depending on the actual purpose for which they are used.

If the hair care preparations according to the invention are supplied as shampoos, these can be clear liquids, opaque liquids (with pearly luster effect), in cream form, gel-like or else in powder form or in tablet form, and as aerosols. The surfactant raw materials on which these shampoos are based can be anionic, cationic, nonionic and amphoteric in nature and also be present in combinations of these substances.

Examples of anionic surfactants suitable for the incorporation into the shampoo preparations according to the present invention are $C_{10-20}$ alkyl- and alkylenecarboxylates, alkyl ether carboxylates, fatty alcohol sulfates, fatty alcohol ether sulfates, alkylolamide sulfates and sulfonates, fatty acid alkylolamide polyglycol ether sulfates, alkanesulfonates and hydroxyalkanesulfonates, olefinsulfonates, acyl esters of isothionates, alpha-sulfo fatty acid esters, alkylbenzenesulfonates, alkylphenol glycol ether sulfonates, sulfosuccinates, sulfosuccinic monoesters and diesters, fatty alcohol ether phosphates, protein-fatty acid condensation products, alkyl monoglyceride sulfates and sulfonates, alkyl glyceride ether sulfonates, fatty acid methyltaurides, fatty acid sarcosinates, and sulforicinoleates. These compounds and their mixtures are used in the form of their salts which are soluble in water or dispersible in water, for example the sodium, potassium, magnesium, ammonium, mono-, di- and triethanolammonium and analogous alkylanunonium salts.

Examples of suitable cationic surfactants are quaternary ammonium salts such as di($C_{10}$-$C_{24}$alkyl)dimethylammonium chloride or bromide, preferably di($C_{12}$-$C_{18}$alkyl)-dimethylammonium chloride or bromide; $C_{10}$-$C_{24}$-alkyldimethylethylammonium chloride or bromide; $C_{10}$-$C_{24}$-alkyltrimethylammonium chloride or bromide, preferably cetyltrimethylammonium chloride or bromide and $C_{20}$-$C_{24}$-alkyltrimethylammonium chloride or bromide; $C_{10}$-$C_{24}$4-alkyldimethylbenzylammonium chloride or bromide, preferably $C_{12}$-$C_{18}$-alkyldimemethylbenzylammoniumchloride; N—($C_{12}$-$C_{18}$-alkyl)pyridinium chloride or bromide, preferably N—($C_{12}$-$C_{16}$-alkyl) pyridinium chloride or bromide; N—($C_{12}$-$C_{18}$-alkyl)isoquinolinium chloride, bromide or monoalkyl sulfate; N—($C_{12}$-$C_{18}$-alkyloylcolaminoformylmethyl)pyridinium chloride; N—($C_{12}$-$C_{18}$-alkyl)-N-methylmorpholinium chloride, bromide or monoalkyl sulfate; N—($C_{12}$-$C_{18}$-alkyl)-N-ethylmorpholinium chloride, bromide or monoalkyl sulfate; $C_{16}$-$C_{18}$-alkylpentaoxethylammonium chloride; isobutylphenoxyethoxyethyldimethyl-benzylammonium chloride; salts of N,N-diethylaminoethylstearylamide and oleylamide with hydrochloric acid, acetic acid, lactic acid, citric acid, phosphoric acid; N-acylamidoethyl-N,N-diethyl-N-methylammonium chloride, bromide or monoalkylsulfate and N-acylaminoethyl-N,N-diethyl-N-benzylammonium chloride, bromide or monoalkyl sulfate, where acyl is preferably stearyl or oleyl.

Examples of suitable nonionic surfactants which can be used as detergent substances are fatty alcohol ethoxylates (alkylpolyethylene glycols); alkylphenol polyethylene glycols; alkyl mercaptan polyethylene glycols; fattyamine ethoxylates (alkylaminopolyethylene glycols); fatty acid ethoxylates (acylpolyethylene glycols); polypropylene glycol ethoxylates (Pluronic); fatty acid alkylolamides (fatty acid amide polyethylene glycols); sucrose esters; sorbitol esters and polyglycol ether.

Examples of amphoteric surfactants which can be added to the shampoos are N—($C_{12}$-$C_{18}$-alkyl)-.beta.-aminopropionates and N—($C_{12}$-$C_{18}$-alkyl)-.beta.-iminodipropionates as alkali metal and mono-, di- and trialkylammonium salts; N-acylamidoalkyl-N,N-dimethylacetobetaine, preferably N—($C_8$-$C_{18}$-acyl)amidopropyl-N, N-dimethylacetobetaine; $C_{12}$-$C_{18}$-alkyldimethylsulfopropylbetaine; amphoteric surfactants based on imidazoline (commercial name: Miranol®, Steinapon®), preferably the sodium salt of 1-(β-carboxymethyloxyethyl)-1-(carboxymethyl)-2-laurylimidazolinium; amine oxide, for example $C_{12}$-$C_{18}$-alkyldimethylamine oxide, fatty acid amidoalkyldimethylamine oxide.

The hair care preparations according to the invention can additionally contain further additives customary in hair care such as for example perfumes, colorants, also those which simultaneously dye or tint the hair, solvents, opacifying agents and pearly luster agents, for example esters of fatty acids with polyols, magnesium and zinc salts of fatty acids, dispersions based on copolymers, thickening agents such as sodium, potassium and ammonium chloride, sodium sulfate, fatty acid alkylolamides, cellulose derivatives, natural rubbers, also plant extracts, protein derivatives such as gelatin, collagen hydrolysates, polypeptides with a natural or synthetic basis, egg yolk, lecithin, lanolin and lanolin derivatives, fats, oils, fatty alcohols, silicones, deodorizing agents, substances with antimicrobial activity, substances with anti-seborrhoeic activity, substances with keratolytic and keratoplastic effect, such as, for example, sulfur, salicylic acid and enzymes as well as further anti-dandruff agents such as olamine, climbazol, zink pyrithion, ketoconazole, salicylic acid, sulfur, tar preparations, derivatives of undecenic acid, extracts of nettel, rosmary, cottonwood, birch, walnut, willow bark and/or arnica.

For the preparation of the hair care preparations the propanediol monoacetate mononitrate is dissolved under stirring at a temperature in the range between 20 and 40° C., preferably at room temperature. Subsequently, the further additives are added.

In the event of alcohol containing scalp respectively hair care preparations propanediol monoacetate mononitrate is dissolved in the alcohol at a temperature in the range between 20 and 40° C., preferably at room temperature. Subsequently, the further additives are added.

In the event of hair rinses and oil-in-water emulsions the active substance is added to the final emulsion below 40° C. under stirring.

The shampoos are produced in a manner known per se by mixing the individual components and where necessary further processing appropriate for the particular type of preparation.

Examples of hair care preparations in which the propanediol monoacetate mononitrate can be used according to the invention and which may be mentioned are hair conditioners, hair tonics and hair regenerating compositions, which are rinsed off from the hair after a certain time or, depending on the formulation, can also remain on the hair. These products contain, inter alia, substances from the group of the above mentioned cationic substances which display a reviving and antistatic property on the hair.

All these preparations are also produced as already mentioned for the shampoo in a manner known per se with the addition of the propanediol monoacetate mononitrate.

The quaternary polymer is preferably selected from e.g. Polyquaternium-6 (e.g. commercialized under the trade name TILAMAR® Quat 640 or 641), Polyquaternium-22 (e.g. commercialized under the trade name TILAMAR® Quat 2240 or 2241), Polyquaternium-7 (e.g. commercialized under the trade name TILAMAR® Quat 710, 711 or 712), etc, The naturally derived conditioning agents are preferably selected from e.g. sugar based polymers such as Guar Hydroxypropyltrimonium Chloride (e.g. commercialized under the trade name Jaguar C-17, Jaguar C-1000, Jaguar C-13S), but not limited hereto.

In principal, any silicone oil is suitable for use in the hair conditioner. However, the silicone oil is preferably selected from dimethicones, dimethiconols, polydimethylsiloxanes, arylated silicones, cyclic silicones, silicone surfactants and aminated silicones and may be volatile or non-volatile. Particular suitable silicone oils are dimethicone, dimethiconol, polydimethylsiloxane which are available from various suppliers such as Dow Corning. The total amount of the at least one silicone oil and/or quaternary polymer and/or naturally derived conditioning agent in the hair conditioner is preferably selected is in the range of 0.01 to 10 wt.-%, preferably 0.02 to 7.5 wt.-%, more preferably 0.05 to 5 wt.-% and most preferably 0.1 to 3 wt.-%, based on the total weight of the composition.

In another preferred embodiment, the cosmetic compositions according to the present invention are O/W emulsions, W/O emulsions and/or gels such as shower gels or hair gels.

In another advantageous embodiment, the cosmetic or pharmaceutical compositions according to the present invention are skin care preparations which in accordance with the invention can be in the form of a liquid, lotion, a thickened lotion, a gel, a cream, a milk, an ointment or a paste.

The cosmetic or pharmaceutical compositions of the invention can also contain further conventional cosmetic adjuvants and additives, such as preservatives/antioxidants, fatty substances/oils, water, organic solvents, silicones, thickeners, softeners, emulsifiers, antifoaming agents, aesthetic components such as fragrances, surfactants, fillers, sequestering agents, anionic, cationic, nonionic or amphoteric polymers or mixtures thereof, propellants, acidifying or basifying agents, dyes, colorings/colorants, abrasives, absorbents, chelating agents and/or sequestering agents, essential oils, skin sensates, astringents, pigments or any other ingredients usually formulated into such compositions.

In accordance with the present invention, the cosmetic or pharmaceutical compositions according to the invention may comprise further cosmetically active ingredients conventionally used in cosmetic or pharmaceutical compositions. Exemplary active ingredients encompass skin lightening agents; agents for the prevention or reduction of inflammation; firming, moisturizing, soothing, and/or energizing agents as well as agents to improve elasticity and skin barrier.

Examples of cosmetic carriers, excipients, ingredients, adjuvants, diluents and additives commonly used in the skin care industry, which are suitable for use in the compositions of the present invention, are for example described in the International Cosmetic Ingredient Dictionary & Handbook by Personal Care Product Council (http://www.personalcarecouncil.org/), accessible by the online INFO BASE (http://online.personalcarecouncil.org/jsp/Home.jsp), without being limited thereto.

The necessary amounts of the active ingredients as well as the cosmetic adjuvants, diluents and additives can, based on the desired product form and application, easily be determined by the skilled person. The additional ingredients can either be added to the oily phase, the aqueous phase or separately as deemed appropriate.

If the cosmetic or pharmaceutical composition according to the invention is an O/W emulsion, then it contains advantageously at least one O/W- or Si/W-emulsifier selected from the list of, Glyceryl Stearate Citrate, Glyceryl Stearate SE (self-emulsifying), stearic acid, salts of stearic acid, polyglyceryl-3-methylglycosedistearate. Further suitable emulsifiers are phosphate esters and the salts thereof such as cetyl phosphate (e.g. as Annphisol® A from DSM Nutritional Products Ltd.), diethanolamine cetyl phosphate (e.g. as Annphisol® DEA from DSM Nutritional Products Ltd.), potassium cetyl phosphate (e.g. as Amphisol K from DSM Nutritional Products Ltd.), sodiumcetearylsulfat, sodium glyceryl oleate phosphate, hydrogenated vegetable glycerides phosphate and mixtures thereof. Further suitable emulsifiers are sorbitan oleate, sorbitan sesquioleate, sorbitan isostearate, sorbitan trioleate, Cetearyl Glucoside, Lauryl Glucoside, Decyl Glucoside, Sodium Stearoyl Glutamate, Sucrose Polystearate and Hydrated Polyisobuten. Furthermore, one or more synthetic polymers may be used as an emulsifier. For example, PVP eicosene copolymer, acrylates/C10-30 alkyl acrylate crosspolymer, and mixtures thereof.

The at least one O/W, respectively Si/W emulsifier is preferably used in an amount of 0.5 to 10 wt. %, in particular in the range of 0.5 to 6 wt.-% such as more in particular in the range of 0.5 to 5 wt.-% such as most in particular in the range of 1 to 4 wt.-%, based on the total weight of the cosmetic or pharmaceutical composition.

Additionally, the cosmetic composition in the form of a O/W emulsion contains advantageously at least one co-emulsifier selected from the list of alkyl alcohols such as Cetyl Alcohol (Lorol C16, Lanette 16) Cetearyl Alcohol (Lanette® O), Stearyl Alcohol (Lanette® 18), Behenyl Alcohol (Lanette® 22), Glyceryl Monostearate, Glyceryl Myristate (Estol® 3650), Hydrogenated Coco-Glycerides (Lipocire Na10) without being limited to this and mixtures thereof.

In a further embodiment, the present invention relates to a process for the preparation of propanediol monoacetate mononitrate, said process encompassing the step of reacting 1,3-propandiol monoacetate with nitrosulfuric acid either in a continuous or in a batch process.

The process according to the present invention is advantageously carried out in an inert solvent or alternatively in the absence of any solvent. As known to a person skilled in the art, the term inert solvent refers to solvents which do not react chemically with the reactants. Particularly suitable inert solvents according to the present invention encompass dichloromethane or chloroform.

The following examples are provided to further illustrate the compositions and effects of the present invention. These examples are illustrative only and are not intended to limit the scope of the invention in any way.

Example 1: Preparation of Propanediol Monoacetate Mononitrate (PDMAMN)

1,3-propandiol monoacetate (PDMA) in dichloromethane (800 g/h, 40%, 2.7 mol PDMA/h) and nitrosulfuric acid (830 g/h, consisting of 2 mol sulfuric acid (98%) per mol of fuming nitric acid, 3.24 mol HNO3/h) were continuously dosed to a microreactor at 0° C. applying a residence time of 11 seconds. Then the mixture is quenched with water (4.1 kg/h) at 15° C. and further neutralised using a sodium hydroxide solution (1.14 kg/h containing 28% NaOH in water). The partially neutralised reaction mixture is collected in a flask for 120 seconds (225 g). The aqueous phase was separated and the organic phase three times washed with water (3×45 ml) and the solvent evaporated in vacuo. Yield: 99% (14.8 g; 98% purity as determined by HPLC).

Example 2 Antimicrobial Efficacy

The antimicrobial efficacy of propanediol monoacetate mononitrate (PDMAMN) is assessed in analogy to the regulatory challenge test method (NF EN ISO11930). The following test solutions were tested 1. Inv 1: 400 mg PDMAMN in 1 ml PEG 400 were diluted with 40 mL physiological serum (0.85% NaCl) containing 7% Ethanol (~1% of PDMAMN)
2. Inv 2: 200 mg PDMAMN in 1 ml PEG 400 were diluted in 40 mL physiological serum (0.85% NaCl) containing 7% Ethanol (~0.5% of PDMAMN)
3. Inv 3: 40 mg 3-PDMAMN in 1 ml PEG 400 were diluted in 40 mL physiological serum (0.85% NaCl) containing 7% Ethanol (~0.1% of PDMAMN)
4. Ref 1: Physiological serum (0.85% NaCl)
5. Ref 2: 1 mL PEG 400+40 mL physiological serum (0.85% NaCl) containing 7% Ethanol
6. Control: 0.5% Phenonip in physiological serum (0.85% NaCl)

All test solutions were deposed in 96-deep well plates (1.6 ml/well). The wells were contaminated with the respective bacterial or the fungal strains as outlined in table $1*10^5$ to $1*10^6$ cfu/ml for the bacteria and $1*10^4$ to $1*10^5$ cfu/ml for the fungi to obtain the initial contamination as outlined in table 1, Zero. After the contamination, each well was thoroughly mixed to ensure a homogeneous distribution of the microorganism. Then each plate was incubated at 22° C. for 24 h. The counting of the (remaining) population was carried out 24 h after contamination.

TABLE 1

|  | Zero | Inv 1 | Inv 2 | Inv 3 | Ref 1 | Ref 2 | Control |
|---|---|---|---|---|---|---|---|
|  |  | colony counts [cfu/ml] |  |  |  |  |  |
| *S. epidermidis* (deo, gram+) | 500000 | 0 | 0 | 0 | 500000 | 400000 | 0 |
| *C. xerosis* (deo, gram+) | 250000 | 0 | 0 | 0 | 250000 | 250000 | 0 |
| *M. furfur* (dandruff, yeast) | 4000 | 0 | 0 | 0 | 40000 | 40000 | 0 |
| *P. Acnes* (acne, gram+) | 100000 | 0 | 0 | 0 | 100000 | 100000 | 0 |

As can be seen in the table above propanediol monoacetate mononitrate exhibits an excellent antimicrobial activity, almost comparable to Phenonip™, a broad spectrum antimicrobial agent designed for preservation of a wide range of cosmetics and toiletries.

The invention claimed is:

1. Propanediol monoacetate mononitrate of formula (I)

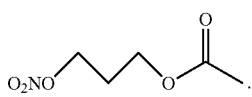

(I)

2. A method to improve preservation of a product by inhibiting microbial degradation thereof, wherein the method comprises adding an anti-microbial effective amount of 1,3-propanediol monoacetate mononitrate to the product.

3. A method to maintain skin homeostasis and/or balance skin microbiome which comprises contacting the skin with an effective amount of 1,3-propanediol monoacetate mononitrate.

4. A deodorant product which comprises 1,3-propanediol monoacetate mononitrate as a deodorant active compound.

5. An anti-acne product which comprises 1,3-propanediol monoacetate mononitrate as an anti-acne agent.

6. A method for treating skin conditions selected from the group consisting of *Pityriasis versicolor*, dandruff formation, seborrheic dermatitis, atopic dermatitis and psoriasis, wherein the method comprises applying to skin in need thereof an effective treatment amount of 1,3-propanediol monoacetate mononitrate.

7. A cosmetic or pharmaceutical composition comprising 1,3-propanediol monoacetate mononitrate.

8. The cosmetic or pharmaceutical composition according to claim 7, wherein the 1,3-propanediol monoacetate mononitrate is an antimicrobial agent.

9. The cosmetic or pharmaceutical composition according to claim 7, wherein the 1,3-propanediol monoacetate mononitrate is an antifungal and/or antibacterial agent.

10. The cosmetic or pharmaceutical composition according to claim 9, wherein the 1,3-propanediol monoacetate mononitrate is an agent that inhibits the growth of microbes selected from the group consisting of *S. epidermis, C. xerosis, M. furfur*, and *P. acnes* and mixtures thereof.

11. The cosmetic or pharmaceutical composition according to claim 7, wherein the 1,3-propanediol monoacetate mononitrate is present in an amount of about 0.005 to 2 wt. %, based on the total weight of the composition.

12. The cosmetic or pharmaceutical composition according to claim 7, wherein the 1,3-propanediol monoacetate mononitrate is present an amount of 0.01 to 1 wt. %, based on the total weight of the composition.

13. The cosmetic or pharmaceutical composition according to claim 7, wherein the 1,3-propanediol monoacetate mononitrate is present in an amount of 0.05 to 0.75 wt. %, based on the total weight of the composition.

14. The cosmetic or pharmaceutical composition according to claim 7, wherein the 1,3-propanediol monoacetate mononitrate is present in an amount of 0.1 to 0.5 wt. %, based on the total weight of the composition.

15. A non-therapeutic method for killing and/or inhibiting growth of microbial cells, wherein the method comprises contacting the microbial cells with an effective amount of 1,3-propanediol monoacetate mononitrate.

16. The method according to claim 15, wherein the microbial cells are fungal and/or bacterial cells.

17. A process for preparing 1,3-propanediol monoacetate mononitrate, wherein the process comprises reacting 1,3-propandiol monoacetate with nitrosulfuric acid.

18. The process according to claim 17, wherein the process is carried out in an inert organic solvent.

* * * * *